United States Patent
March et al.

(10) Patent No.: US 6,524,298 B1
(45) Date of Patent: *Feb. 25, 2003

(54) THERAPEUTIC AND DIAGNOSTIC AGENT DELIVERY

(75) Inventors: Keith L. March, Carmel, IN (US); Michael Aita, Sunnyvale, CA (US); Randy Kesten, Mountain View, CA (US); Craig Smith, Bronxville, NY (US)

(73) Assignee: CardioGenesis Corporation

( * ) Notice: Subject to any disclaimer, the term of this patent is extended or adjusted under 35 U.S.C. 154(b) by 0 days.

This patent is subject to a terminal disclaimer.

(21) Appl. No.: 09/794,270

(22) Filed: Feb. 27, 2001

Related U.S. Application Data

(62) Division of application No. 09/304,802, filed on May 4, 1999, now Pat. No. 6,224,584, which is a division of application No. 09/107,079, filed on Jun. 29, 1998, now Pat. No. 5,997,525, which is a continuation of application No. 08/483,512, filed on Jun. 7, 1995, now Pat. No. 5,840,059.

(51) Int. Cl.[7] ............................................. A61M 31/00
(52) U.S. Cl. ...................................... 604/508; 604/507
(58) Field of Search ........................ 606/41, 42, 45–52, 606/7, 15, 192, 194; 607/100–102, 104, 106, 115, 116, 122, 131, 89, 119, 120; 604/95.01, 28, 22, 507, 508; 600/374

(56) References Cited

U.S. PATENT DOCUMENTS

| | | | |
|---|---|---|---|
| 5,840,059 A | | 11/1998 | March et al. .................. 604/53 |
| 5,921,982 A | * | 7/1999 | Lesh et al. ..................... 606/41 |
| 5,997,525 A | | 12/1999 | March et al. ................ 604/508 |

FOREIGN PATENT DOCUMENTS

| WO | WO 94/21237 | 9/1994 |
|---|---|---|

OTHER PUBLICATIONS

Guzman, Raul J., et al., "Efficient Gene Transfer into Myocardium by Direct Injection of Adenovirus Vectors," Circulation Research, vol. 73, No. 6, pp. 1202–1207, 1993.

Acsadi, Gyula, et al., "Direct Gene Transfer and Expression into Rat Heart in Vivo," The New Biologist, vol. 3, No. 1, pp. 71–81, Jan., 1991.

Lynch, Carmel. M., et al., "Long–term expression of human adenosine deaminase in vascular smooth muscle cells of rats: A model for gene therapy," Proc. Natl. Acad. Sci., U.S.A., vol. 89, pp. 1138–1142, Feb., 1992.

March, Keith L.., et al., "Pharmacokinetics of Adenoviral Vector–Mediated Gene Delivery to Vascular Smooth Muscle Cells: Modulation by Poloxamer 407 and Implications for Cardiovascular Gene Therapy," Human Gene Therapy, vol. 60, pp. 41–53, Jan., 1995.

(List continued on next page.)

Primary Examiner—Manuel Mendez
(74) Attorney, Agent, or Firm—Gibson, Dunn & Crutcher LLP

(57) ABSTRACT

A system for treating a patient's heart which comprises a means to form channels in the heart wall and a means to deliver a therapeutic or diagnostic agent into the channels. Additionally, the system may comprise a means to retain the agent within the channels for a useful period of time. The system may be configured to be introduced percutaneously or intraoperatively. The system generally comprises an elongated, flexible lasing transmission means having a laser radiation emitting means and an delivery lumen opening at the distal end. Practice of the invention comprises forming channels in the heart wall and delivering a therapeutic or diagnostic agent into the channel. Gene therapy agents of this invention comprise vectors for transferring genetic information to the heart tissue in vivo or harvested cells which have been genetically engineered in vitro. Additionally, the invention may comprise retaining the agent within the channels, for example, by incorporating the agent in a viscous carrier.

9 Claims, 2 Drawing Sheets

OTHER PUBLICATIONS

Dichek, David A., et al., "Seeding of Intravascular Stents with Genetically Engineered Endothelial Cells," Circulation, vol. 80, No. 5, pp. 1347–1353, Nov., 1989.

Plautz, Gregory, M.D., et al., "Introduction of Vascular Smooth Muscle Cells Expressing Recombinant Genes in Vivo," Circulation, vol. 83, No. 2, pp. 578–583, Feb., 1991.

French, Brent A., et al., "Direct in Vivo Gene Transfer into Porcine Myocardium Using Replication–Deficient Adenoviral Vectors," Circulation, vol. 90, No. 5, pp. 2414–2424, Nov., 1994.

Lin, Hua, M.D., et al., "Expression of Recombinant Genes in Myocardium in Vivo After Direct Injection of DNA," Circulation, vol. 82, No. 6, pp. 2217–2221, Dec. 1990.

Flugelman, Moshe Y., M.D., et al., "Low Level in Vivo Gene Transfer into the Arterial Wall Through a Perforated Balloon Catheter," Circulation, vol. 85, No. 3, pp. 1110–1117, Mar., 1992.

Nabel, Elizabeth, G., et al., "Recombinant Gene Expression in Vivo Within Endothelial Cells of the Arterial Wall," Science, vol. 244, pp. 1342–1344, Jun. 16, 1989.

Wilson, James M., et al., "Implantation of Vascular Grafts Lined with Genetically Modified Endothelial Cells," Science, vol. 244, pp. 1344–1346, Jun. 16, 1989.

Leclerc, Guy, et al., "Percutaneous Arterial Gene Transfer in a Rabbit Model," J. Clin. Invest., vol. 90, pp. 936–944, 1992.

Nabel, Elizabeth G., et al., "Site–Specific Gene Expression in Vivo by Direct Gene Transfer into the Arterial Wall," Science, vol. 249, pp. 1285–1288, Sep. 14, 1990.

* cited by examiner

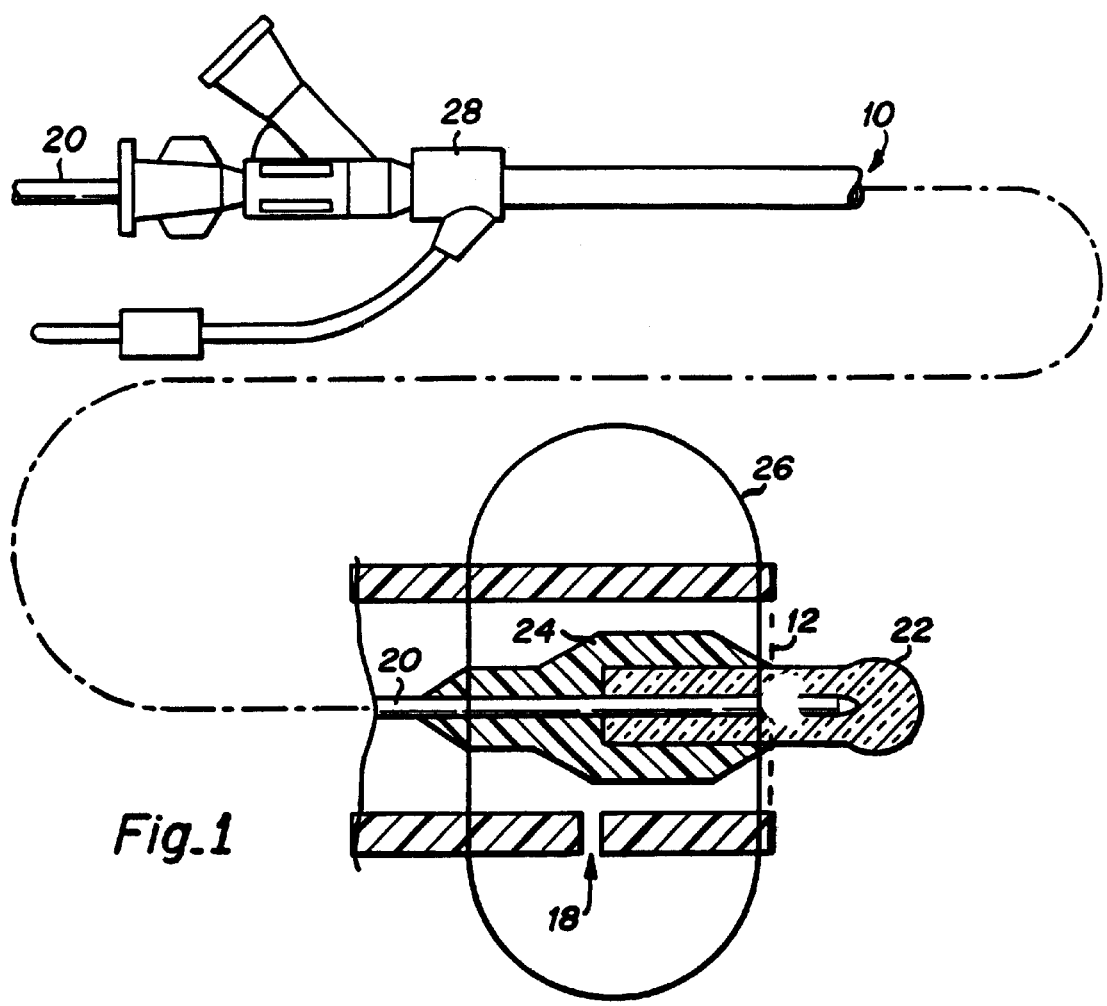
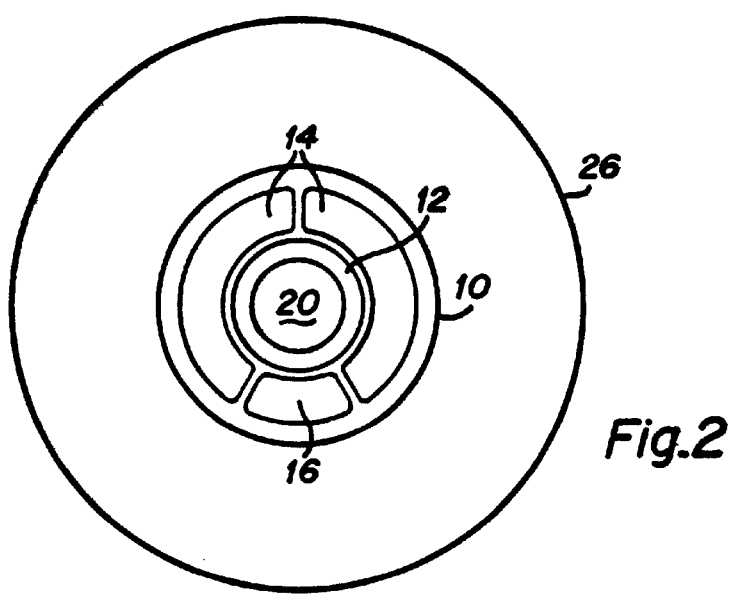

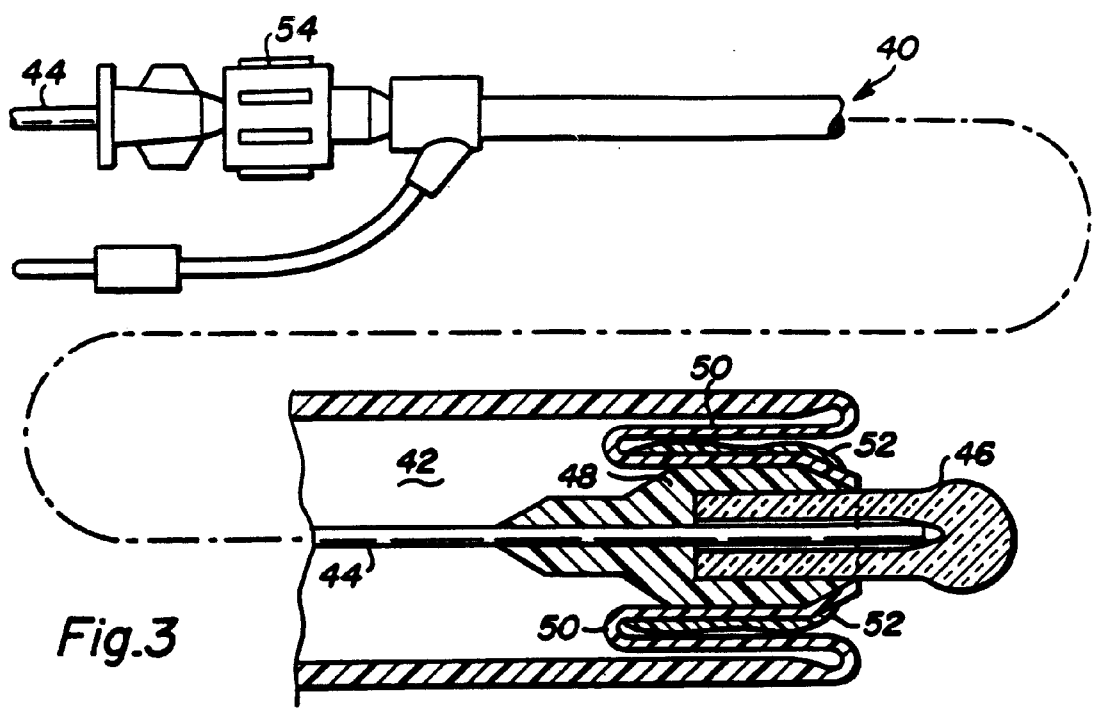
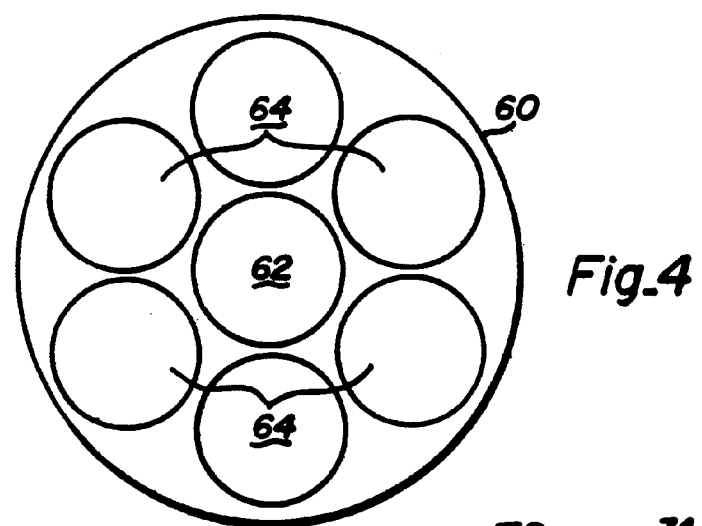
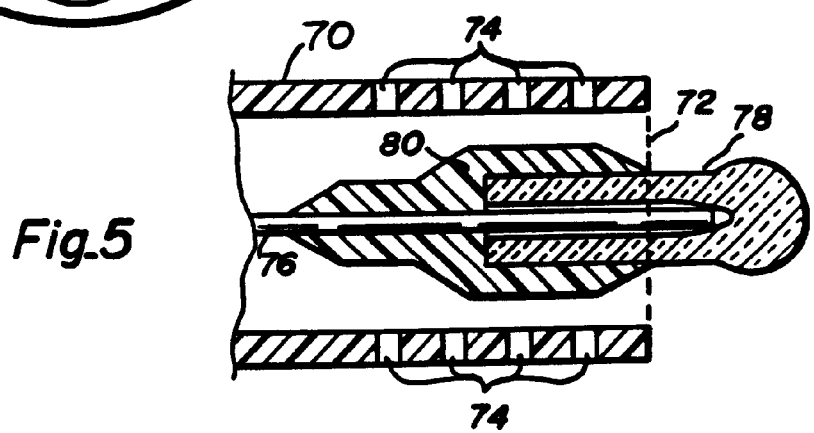

THERAPEUTIC AND DIAGNOSTIC AGENT DELIVERY

This application is a divisional application of U.S. patent application Ser. No. 09/304,802, filed May 4, 1999 now U.S. Pat. No. 6,224,584 allowed, which is a divisional application of U.S. patent application Ser. No. 09/107,079, filed Jun. 29, 1998, now U.S. Pat. No. 5,997,525, which is a continuation of parent application U.S. patent application Ser. No. 08/483,512, filed Jun. 7, 1995, now U.S. Pat. No. 5,840,059.

BACKGROUND OF THE INVENTION

This invention is directed to a method and system for treating a patient's heart with therapeutic or diagnostic agents. More particularly, it involves a means to form channels in desired layers of the heart muscle, the epicardium, endocardium and myocardium, and means to deliver therapeutic or diagnostic agents into the channels.

Targeted delivery of therapeutic or diagnostic agents is a desirable but often difficult goal. Potential benefits include efficient use of the agent and limitation of agent action to the desired area. However, the problems that must be overcome are significant: access, transporting the agent to the desired area of the patient; minimization of systemic loss, keeping the agent within the desired area; and timing, ensuring a sufficient quantity of the agent is available in the desired area for sufficient period of time to achieve the therapeutic or diagnostic effects.

One promising strategy for agent delivery involves somtatic gene therapy. Cells in a desired region of the body are engineered to express a gene corresponding to a therapeutically or diagnostically useful protein. Genetic information necessary to encode and express the protein is transferred to the cells by any of a number of techniques, including viral vectors, electroporation, receptor-mediated uptake, liposome masking, precipitation, incubation and others. Gene therapy can be a direct in vivo process where genetic material is transferred to cells in the desired region of the patient's body. Most current in vivo strategies rely on viral vectors. Alternatively, the process can be an indirect in vitro process where cells from the desired region are harvested, genetic material is transferred to the cells, and the cells are implanted back in the patient's body. In vitro techniques allow for more flexibility in transfer methods and may be safer since viral vectors need not be introduced into the patient's body, thus avoiding the theoretical risk of insertional mutations, replication reactivation and other harmful consequences. However, not all tissues are susceptible to harvesting and implantation and require an in vivo technique. The engineered cells can secrete the protein for a significant period of time, ensuring its supply in the target region. Human adenosine deaminase was expressed in vivo by rat vascular smooth muscle cells for over six months. Lynch C M et al., *Proc. Natl. Acad. Sci. USA* 89:1138–42 (1992).

One region of interest for gene therapy is the circulatory system. Researchers have transferred genetic material to the vascular walls, particularly the smooth muscle and endothelial cells. Suitable delivery techniques include ligation of the vessel (Lynch et al., supra.), dual-balloon catheters (Leclerc G et al., *J. Clin. Invest.* 90:936–44 (1992)), perforated balloon catheters (Flugelman M Y et al., *Circulation* 85:1110–17 (1992)), stents seeded with transduced endothelial cells (Dichek D A et al., *Circulation* 80:1347–53 (1989)) and vascular grafts lined with transduced endothelial cells (Wilson J M et al., *Science* 244:1344–46 (1989)).

However, these methods have not been found suitable for treatment of the heart muscle. Thus far, experimental gene therapy in rats has been achieved through direct injection of DNA into the myocardium. Lin H et al., *Circulation* 82:2217–21 (1992) and Acsadi G et al., *New Biologist* 3:71–81 (1991). In these studies, direct injection caused inflammation, apparent myocyte necrosis and scar tissue along the needle tracks. When compared to injection of plasmid DNA, gene transfer by injection of adenovirus vectors was markedly more efficient. Guzman R G et al., *Circulation Research* 73:1202–7 (1993). Gene transfer using adenovirus vectors injected into pig hearts was highly efficient in regions immediately adjacent the injection, but evidence of gene transfer was found only within 5 mm of the injection. French B A et al., *Circulation* 90:2414–24 (1994). As in the studies above, a prominent inflammatory response was associated with the injection. There remains a need for effective gene therapy methods for the heart.

Another difficulty associated with gene therapy is the need to transfer an effective amount of the genetic material in a clinically relevant time period. Exemplary techniques for introduction of engineered endothelial or smooth muscle cells or for in vivo gene transfer require total occlusion of the vessel for 30 minutes. Nabel E G et al., *Science* 249:1285–88 (1990); Nabel E G et al., *Science* 244:1342–44 (1989); and Plautz G et al., *Circulation* 83:578–83 (1991). These time frames would not be feasible for delivery involving the heart. A study attempting to shorten these times employed a perforated balloon catheter and successfully delivered retroviral vectors within one minute, but achieved fewer than 100 transduced cells in a two cm segment of tissue. Flugelman et al., supra. Accordingly, there remains a need to provide gene therapy methods that effect sufficient cellular transduction either by providing more rapid transfer rates or by allowing long-term delivery without impermissibly interfering with cardiac function.

Targeted agent delivery that does not rely on gene therapy would also benefit from similar features. It is often desirable to release the therapeutic or diagnostic agent over a period of time. Levy R J et al., WO 94/21237 discloses a system and method for treatment of arrhythmia that involves transmyocardial delivery of time-release antiarrthymic agents by contacting the epicardium, endocardium or pericardium. Levy et al.'s drug compositions generally comprise a biocompatible polymer formulated to release the active agent in a controlled manner, preferably in the form of a patch applied to the exterior of the heart. The reference also suggests various intravascular placement methods including an implantable catheter tip, an expandable system with anchoring prongs or intramyocardial placement via a stab wound with a trocar. Thus, there is also a need for a system for cardiac agent delivery that effectively delivers agent to the heart wall.

SUMMARY OF THE INVENTION

This invention is a system for treating a patient's heart which comprises a means to form channels in the heart wall and a means to deliver a therapeutic or diagnostic agent into the channels. Additionally, the system may comprise a means to retain the agent within the channels for a useful period of time. The system may be configured to be introduced percutaneously for intravascular delivery to form channels from the epicardial surface. Alternatively, the system may be configured for intraoperative use, to be introduced thoracoscopically or through a thoracotomy, to form transmural channels from the epicardial surface. The system generally comprises an elongated, flexible lasing transmission means having a laser radiation emitting means and an agent delivery means on the distal end.

In one embodiment, the system comprises a catheter having an optical fiber with a lens at the distal end disposed in a first lumen, an agent delivery lumen having an opening at the distal end of the catheter and an occlusion balloon disposed adjacent the distal end of the catheter in fluid communication with an inflation lumen. In use, the distal end of the catheter is positioned adjacent a desired area of the heart wall, then radiation is transmitted through the optical fiber and emitted through the lens to form a channel in the myocardium. The distal end of the catheter is advanced into the channel and the occlusion balloon inflated. The agent is introduced into the channel through the delivery lumen and is retained by the occlusion balloon.

In another embodiment, the system comprises an optical fiber with a lens at tire distal end slidably disposed within a catheter. The distal end of the catheter is connected to the distal end of the fiber by a flexible tube which presents a delivery surface. Agent is coated along the outside of the tube. In preparation for delivery, the optical fiber is moved proximally relative to the catheter to cause the tube to invert, shielding the agent. Once the channel is formed, the optical fiber is moved distally relative to the catheter to evert the delivery surface of the flexible tube. In such embodiments, the means to retain the agent within the channel for a useful period of time may comprise use of a viscous carrier, such as a biocompatible polymer matrix or a carrier which can become or be made highly viscous in situ to affect the kinetics of the agent and host cell interaction to improve the efficacy of the agent.

In another embodiment, the system comprises a multi-lumen catheter having a central agent delivery lumen and a plurality of lumens positioned radially around the central lumen, having an optical fiber with a lens on the distal end disposed in each.

In yet another embodiment, the system comprises a catheter with a optical fiber having a lens on the distal end disposed within a lumen. The lumen is sealed at the distal end and has a plurality of delivery ports on the catheter's sidewall adjacent the distal end which are in fluid communication with the lumen. Once the distal end of the catheter has penetrated the heart wall, agent is delivered through the lumen and out the ports.

Practice of the invention comprises forming channels in the heart wall and delivering a therapeutic or diagnostic agent into the channel. Gene therapy agents of this invention comprise vectors for transferring genetic information to the heart tissue in vivo or harvested cells which have been genetically engineered in vitro. Additionally, the invention may comprise retaining the agent within the channels, for example, by incorporating the agent in a viscous carrier.

Channel forming means other than laser radiation transmitting means are suitable. Examples of useful means include thermal ablation means, radiofrequency ablation means, rotating tissue removal means, water jet removal means and ultrasonic ablation means.

BRIEF DESCRIPTION OF THE DRAWINGS

FIG. 1 is an elevational view, partially in section, of a catheter with an occlusion balloon.

FIG. 2 is a cross-section of the catheter shown in FIG. 1, taken through the occlusion balloon.

FIG. 3 is an elevational view, partially in section, of a catheter comprising a delivery tube.

FIG. 4 is a cross-sectional view of a multilumen catheter useful in the practice of the invention.

FIG. 5 is an elevational view, partially in section, of a distal portion of a catheter comprising perfusion ports.

DETAILED DESCRIPTION OF THE INVENTION

Referring to FIG. 1, an embodiment of the invention comprises an elongated catheter 10 having an optical fiber lumen 12 opening at the distal end of the catheter, two delivery lumens 14 (shown in FIG. 2) also opening at the distal end of the catheter and an inflation lumen 16 (shown in FIG. 2) in fluid communication with inflation port 18 located in the sidewall of catheter 10 adjacent the distal end. The channel forming means, comprising optical fiber 20, is disposed in lumen 12. Lens 22 is attached to lens capsule 24 which is in turn bonded to the distal end of optical fiber 20. Suitable optical fiber and lens configurations may be found in U.S. Pat. No. 5,093,877, which is hearby incorporated in its entirety by reference. Other configuration are also suitable. Occlusion balloon 26 (shown in phantom) is secured adjacent the distal end of catheter 10 and is in fluid communication with inflation lumen 16 through ports 18. Preferably, balloon 26 is formed from an elastomeric material, such as latex or polyurethane, so that it conforms tightly to the catheter when in an uninflated condition. At the proximal end of catheter 10 is a conventional multi arm adapter 28 for providing access to delivery lumens 14 and inflation lumen 16. Optical fiber 20 extends out the proximal end of adapter 28 and is conventionally connected to a laser radiation source (not shown). FIG. 2 is a cross-sectional view of catheter 10, taken through balloon 26.

In use, catheter 10 is percutaneously introduced by means of conventional cut down techniques in the patient's arterial system, generally through the femoral artery. A guiding or shielding catheter (not shown) may be employed to facilitate introduction of the distal end of catheter 10 into the patient's left ventricle. Lens 22 is positioned in contact against a desired region of the endocardium. Laser energy is delivered in a burst or a series of bursts through the optical fiber 20 and lens 22 to form a channel through the endocardium and into the myocardium. The distal end of catheter 10 is advanced into the channel and fluid is introduced into inflation lumen 16 to inflate balloon 26. Therapeutically or diagnostically useful agent is then introduced into delivery lumen 14 and ejected into the channel. Inflated balloon 26 occludes the proximal portion of the channel to prevent backflow and help maintain the agent in the channel. Preferably, catheter 10 is left in place with balloon 26 inflated for about 10 to about 300 seconds to capture the agent within the channel and allow it to diffuse into the myocardium. Depending on the characteristics of the agent, the occlusion balloon may not be required if the agent is rapidly absorbed into the myocardium or if the agent has rapid effect and catheter 10 may be configured without one.

FIG. 3 illustrates an alternate embodiment comprising catheter 40 having a lumen 42. The channel forming means, comprising optical fiber 44, is disposed in lumen 42. Lens 46 is attached to lens capsule 48 which is in turn bonded to the distal end of optical fiber 44. Delivery tube 50 is formed of a flexible material and has a proximal end secured to a distal portion of catheter 40 and a distal end secured of lens capsule 48. When capsule 48 is positioned substantially flush with the distal end of catheter 40, delivery tube 50 is inverted, shielding the outer surface 52 of tube 50. Moving optical fiber 44 and capsule 48 distally relative to catheter 40 causes delivery tube 50 to evert, exposing surface 52. Pressurized fluid can also be introduced into lumen 42 to facilitate or cause the eversion of delivery tube 50. At the proximal end of catheter 40 is adapter 54 which may be configured to permit the introduction of pressurized fluid into lumen 42. Optical fiber 44 extends out the proximal end of adapter 54 and is conventionally connected to a laser radiation source (not shown).

In use, the therapeutically or diagnostically useful agent is applied to the everted surface 52 which is then inverted to shield the agent during delivery. In these embodiments, the agent preferably should have sufficient viscosity to adhere to surface 52. Suitable viscosity enhancing means are described below. A channel in the heart wall is formed as described above, by transmitting energy through fiber 44. Catheter 40 may be sized so that the distal end will not enter the channel so that when fiber 44 is further advanced, delivery tube 50 will evert. As described above, pressurized fluid may be introduced into lumen 42 to facilitate the eversion. Alternatively, pressurized fluid alone, fixing the proximal end of catheter 40 while advancing fiber 44 or other suitable means may be used to cause the eversion. Everting delivery tube 50 to expose surface 52 delivers the agent to the walls of the channel. The catheter is held in place for a suitable period of time, such as about 10 to about 300 seconds, allowing the agent to diffuse into the myocardium. The viscosity of the agent also helps retain the agent in the channel.

A cross-section of an alternate embodiment is shown in FIG. 4. Catheter 60 has central lumen 62 with six radial lumens 64. Optical fibers with lens and capsule assemblies may be disposed in radial lumens 64, leaving central lumen 62 for delivering the agent. Catheter 60 could also be fitted with an occlusion balloon. Similar embodiments comprise different patterns of delivery lumens and optical fiber lumens. Use of catheter 60 generally follow the steps detailed above.

Yet another embodiment is shown in FIG. 5. Catheter 70 has lumen 72 in fluid communication with a plurality of perfusion ports 74 through the sidewall of catheter 70 adjacent its distal end. Optical fiber 76 is disposed in lumen 72, with the distal end attached to lens 78 by lens capsule 80 bonded to fiber 76. Lumen 72 is sealed around lens capsule 80 at the distal end of catheter 70. Use of catheter 70 is generally as for the above embodiments. After forming the channel, the distal end of catheter 70 is advanced into the channel. The therapeutically or diagnostically useful agent is introduced under pressure into lumen 72 and exits through perfusion ports 74. In a similar embodiment, a distal portion of catheter 70 is provided with a woven or otherwise permeable material (not shown) instead of the perfusion ports. The agent will then seep out the material at the distal portion of the catheter and permeate into the heart wall. It is believed that the weeping delivery may facilitate the diffusion of the agent into the tissue.

It is believed that abrasion to the wall of the channels may aid in absorption of the agent. Accordingly, it may be desirable to configure the catheters of the invention so as to allow selective abrasion.

One of skill in the art would recognize that each of these embodiments could be easily configured for a device where access to the heart is gained intraoperatively, by sub-xiphoid entry or through a thoracotomy, or by open heart surgery. Preferably, the thoracotomy should be minimal, through an intercostal space. Thoracoscopic, fluoroscopic or ultrasonic visualization may be employed to facilitate the procedure.

Gene therapy agent is introduced into the pericardial space, the device is removed and the penetration of the pericardium may be sutured or closed in other suitable manner to seal in the agent.

The system and method of this invention may employ a wide variety of agents ranging from active compounds to markers to gene therapy compounds. Active compounds may comprise vascular endothelial growth factor (VEGF), acidic and basic fibroblast growth factors (aFGF, bFGF), angiogenin, nitric oxide, prostaglandin, prostaglandin synthase and other prostaglandin synthetic enzymes and isoforms of superoxide dismutase and other antioxidant proteins.

Gene therapy agents may comprise naked DNA or DNA compositions for delivery of genetic information in vivo or cells which have been genetically modified in vitro. Methods for transfer of genetic information generally fall into one of three categories. First, DNA may be delivered by physical means, including microinjection, electroporation, biobalistic or particle bombardment, jet injection, and others. Second, DNA may be delivered by chemical means, using calcium phosphate, DEAE dextran, polylysine conjugates, "starburst" dendrimer conjugates, polybrene-dimethyl sulfoxide, receptor-mediated uptake systems such as asialoglycoprotein and transferrin, liposomes, virion like particles (VLP's), intra-cellular targeting ligands and others. Third, DNA may be delivered by biological means, including retroviral vectors such as Moloney murine leukemia virus (MoMLV), adenovirus vectors and adeno-associated virus vectors (AAV), herpes simplex virus vectors, semliki forest virus vectors, sindbis virus vectors and others. Adenoviral vectors would include first-generation deletion mutant vectors as well as second, third and higher generation vectors. The other vectors similarly may be sub-categorized and each are considered useful agents for the practice of the invention. Combinations of the above methods may also be useful. A preferred embodiment of the invention comprises delivering a replication-deficient, first generation adenvovirus vector (Av1) expressing fibroblast growth factor 5 into the pericardial space. Selection of an in vitro or in vivo technique depends in part upon the type of treatment desired. Retroviral vectors typically require dividing cells for efficient transfer and are not available in titers as high as adenoviral vectors. However, retroviral vectors insert the genetic information into the host DNA which can result in stable integration into the genome. Adenovirus vectors express the transferred gene in a non-integrating fashion. Accordingly, selection between the two vectors may depend in part on whether the desired activity is to be acute or chronic and the nature of the target tissue.

Successful in vivo transfer or integration of modified cells turn the epicardium or pericardium into a secreting organ capable of expressing the desired genetic information. Examples of useful therapeutic genes are angiogenic factors such as vascular endothelial growth factor (VEGF), acidic and basic fibroblast growth factors (aFGF, bFGF) and angiogenin. These factors are useful for enhancing collateral formation of vasculature by inducing angiogenesis to relatively ischemic areas of myocardial tissue. Other useful genes are those responsible for controlling nitric oxide production such as nitric oxide synthase. Such genes could be used to reduce the restenotic response or enhance the vasodilation response. Control of vasodilation may permit treatment of angina. The effects of nitric oxide on neural conduction and action potentials may be exploited to modulate arrhythmogenesis. Genes expressing prostaglandin sythetic enzymes such as prostaglandin synthase may be used to effect local generation of prostaglandins to influence neural conduction and cardiac arrhythmogenesis, as well as causing vasodilation and reducing vascular proliferation following injury. Yet other useful genes include those expressing isoforms of superoxide dismutase and other antioxidant proteins. These genes could confer protection in the case of myocardial ischemia. One of skill in the art will recognize that many other genes may be useful in the practice of this invention.

Generally, a vector should be delivered at a concentration of between about $10^6$ and about $10^{10}$ infectious units/ml and preferably between about $10^8$ and about $10^9$ infectious units/ml of carrier fluid. Useful concentrations for other gene therapy agents as well as other therapeutic and diagnostic agents will vary considerably, however suitable concentration for the particular agent can be determined by one of skill in the art.

When desired, the agent may be delivered in a form to keeps the agent associated with the target tissue for a useful period of time, such as with a viscosity-enhancing to produce a thixotropic gel. When the agent comprises a gene transfer means, the securing agent must retain the agent in proximity with the target tissue to provide efficient gene transfer. Useful times are dependent upon the agent used.

In certain embodiments, particularly when using catheter 40, the therapeutic or diagnostic agent is mixed with a viscous biocompatible polyol to maintain prolonged, high concentration of the agent in the channels and affect the kinetics of the agent-target cell interaction. For example, poloxamer 407 combined with an Av1 vector achieves high rates of transduction in bovine aortic smooth muscle cells. March K L et al., "Pharmacokinetics of Adenoviral Vector-Mediated Gene Delivery to Vascular Smooth Muscle Cells: Modulation by Poloxamer 407 and Implications for Cardiovascular Gene Therapy," *Human Gene Therapy* 6:41–53 (1995).

Alternatively, a catheter could be employed to deliver an agent incorporated in a biocompatible polymer matrix. Suitable polymeric materials may comprise polyurethane, polydimethylsiloxane, ethylene vinyl acetate, polymethyl methacrylate, polyamide, polycarbonate, polyester, polyethylene, polypropylene, polystyrene, polyvinyl chloride, polytetrafluoroethylene and cellulose acetate or a mixture of the above or copolymers. These non-biodegradable polymers may be employed as hollow reservoirs or other structures. Additionally, pharmacologically inert fillers may be employed to tailor the time release characteristics of the agent. Such filler may comprise polyethylene glycol, inulin, dimethyl tartrate or others. Suitable biodegradeable polymers comprise collagen, polylactic-polyglycolic acid and polyanhydride. In these embodiments, the agent is dispersed in a polymer which is configured to degrade over a useful period of time, releasing the agent. Various means for employing polymer compounds to secure a therapeutic agent are disclosed in Levy et al., WO 94/2123 and in U.S. application, Ser. No. 08/033,307, filed Mar. 15, 1994, which is hereby incorporated by reference.

In other embodiments, a biocompatible material could be delivered to seal and retain the agent within the channel. In the embodiments detailed above, one of the delivery lumens could be employed to deliver a sealing agent after delivery of the agent.

What is claimed is:

1. A method of treating the heart comprising:

a) ablating the heart wall with radio frequency energy;

b) delivering a tissue altering agent to the heart wall; and c) delivering an angiogenic agent within the heart wall.

2. The method of claim 1 wherein the tissue altering agent effects restenosis.

3. The method of claim 1 wherein the angiogenic agent of step c) is in combination with a next tissue altering agent.

4. The method of claim 1 further comprising step d) using a retaining element to retain the angiogenic agent within the channels for a useful period of time.

5. The method of claim 1 wherein the angiogenic agent of step c) is in combination with a time release agent.

6. The method of claim 1 further comprising step d) sealing the therapeutic agent within the heart wall with a sealing agent.

7. The method of claim 5 wherein the retaining element is a biocompatible polymer incorporating the angiogenic agent.

8. The method of claim 1 wherein the angiogenic agent of step b) is in combination with a time release agent.

9. The method of claim 1 further comprising step c) sealing the therapeutic agent within the heart wall with a sealing agent.

* * * * *